(12) United States Patent
Stuart et al.

(10) Patent No.: US 9,606,707 B1
(45) Date of Patent: Mar. 28, 2017

(54) USER INPUT METHODOLOGY FOR TOGGLE ITEMS

(71) Applicant: ALLSCRIPTS SOFTWARE, LLC, Chicago, IL (US)

(72) Inventors: Anthony Edward Stuart, Wake Forest, NC (US); Ross Carlyle Teague, Cary, NC (US)

(73) Assignee: ALLSCRIPTS SOFTWARE, LLC, Chicago, IL (US)

( * ) Notice: Subject to any disclaimer, the term of this patent is extended or adjusted under 35 U.S.C. 154(b) by 289 days.

(21) Appl. No.: 14/557,458

(22) Filed: Dec. 2, 2014

(51) Int. Cl.
| | | |
|---|---|---|
| *G06F 17/00* | (2006.01) | |
| *G06F 3/00* | (2006.01) | |
| *G06F 3/048* | (2013.01) | |
| *G06F 3/0484* | (2013.01) | |
| *G06F 3/0481* | (2013.01) | |
| *G06F 3/0482* | (2013.01) | |

(52) U.S. Cl.
CPC ........ *G06F 3/04842* (2013.01); *G06F 3/0482* (2013.01); *G06F 3/04812* (2013.01)

(58) Field of Classification Search
CPC . G06F 3/0482; G06F 3/04842; G06F 3/04812
See application file for complete search history.

(56) References Cited

U.S. PATENT DOCUMENTS

| | | | | |
|---|---|---|---|---|
| 7,554,521 B1* | 6/2009 | Migos | ................. | G06F 3/04847 345/156 |
| 7,971,155 B1* | 6/2011 | Yoon | ..................... | G06F 3/0482 715/843 |
| 2003/0085881 A1* | 5/2003 | Bosma | .................. | G06F 3/0481 345/173 |
| 2003/0095153 A1* | 5/2003 | Bosma | .................. | G06F 3/0486 715/859 |
| 2003/0210282 A1* | 11/2003 | Bosma | .................. | G06F 3/0486 715/845 |
| 2004/0111673 A1* | 6/2004 | Bowman | ............... | G06F 9/4443 715/234 |
| 2004/0119742 A1* | 6/2004 | Silbey | ................... | G06F 3/0481 715/760 |
| 2004/0196316 A1* | 10/2004 | Handy Bosma | ...... | G06F 3/0486 715/821 |
| 2005/0125744 A1* | 6/2005 | Hubbard | ............... | G06F 3/0482 715/824 |
| 2006/0161889 A1* | 7/2006 | Stabb | .................. | G06F 9/45512 717/113 |

(Continued)

*Primary Examiner* — Jordany Nunez
(74) *Attorney, Agent, or Firm* — Tillman Wright, PLLC; Chad D. Tillman; Jeremy C. Doerre

(57) ABSTRACT

A method for facilitating editing of a toggle item includes displaying an interface comprising one or more toggle items, each toggle item being configured to be toggled on and off when clicked on; receiving input corresponding to movement of a pointer to be disposed over a first toggle item of the one or more toggle items; determining that a predetermined amount of time has passed with the pointer being disposed over the first toggle item; displaying a cursor in the first toggle item at the location of the pointer; receiving input corresponding to a click while the cursor is displayed in the first toggle item; receiving input corresponding to editing of the first toggle item; and updating, based on the input corresponding to editing of the toggle item, the text of the toggle item.

17 Claims, 11 Drawing Sheets

(56) References Cited

U.S. PATENT DOCUMENTS

| | | | |
|---|---|---|---|
| 2009/0037831 A1* | 2/2009 | Best | G06F 9/4443 715/764 |
| 2009/0094553 A1* | 4/2009 | Karstens | G06F 3/04817 715/810 |
| 2009/0172576 A1* | 7/2009 | Cheaz | G06F 9/4443 715/765 |
| 2010/0115454 A1* | 5/2010 | Tuli | H04L 67/04 715/780 |
| 2012/0290946 A1* | 11/2012 | Schrock | G06Q 10/107 715/752 |
| 2016/0026374 A1* | 1/2016 | Schulz | G06F 3/04847 715/212 |

* cited by examiner

FIG. 2

FRANK BLACK

Barton, Jason Jr. (Mr.)
August 17, 1950 (63y) | Sex M | MRN 933145526

Vitals
Measurements
Labs

Encounter (11/28/2014)

Patient presents with: Fever *Chills* *Body Aches*

Patient was last seen:
*Less than 1 month ago*
*More than 1 month ago*
*More than a year ago*

Next

Barton, Jason Jr. (Mr.)
August 17, 1950 (63y) | Sex M | MRN 933145526

Vitals
Measurements
Labs

Encounter (11/28/2014)

Patient presents with:   Fever   *Chills*   *Body Aches*

Patient was last seen:
*Less than 1 month ago*
*More than 1 month ago*
More than a year ago

Next

FRANK BLACK

USER INPUT METHODOLOGY FOR TOGGLE ITEMS

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

The present invention generally relates to interfaces for facilitating user input, and, more specifically, to such interfaces for use in a healthcare application.

Toggle interactions are useful interface tools. They allow users to see all their choices at once, they can be presented in a 'narrative' format as part of a sentence or paragraph, and they allow for easy "on/off" (or change between multiple states) if the user makes a mistake or wants to quickly change the input. Due to their usefulness in a narrative text description, there is the potential to want to edit or add free text as part of an item that can be toggled. The problem with this is that the fastest, most desired method to insert a cursor to add free text is to click on the location for the cursor. With a toggle item, a click toggles the item to another state and doesn't allow you to drop in the cursor. Solutions for adding free text to an item have included right clicking on the toggle item to reveal a menu with an "edit" choice which will put the toggle item into 'text edit' mode, and removing the toggle function of the item once it has been selected (which allows you to add free text but doesn't allow you to change your mind after a click on the toggle item).

A need exists for improvement in interfaces for facilitating user input. This, and other needs, are addressed by one or more aspects of the present invention.

SUMMARY OF THE INVENTION

The present invention includes many aspects and features. Moreover, while many aspects and features relate to, and are described in, the context of healthcare applications, the present invention is not limited to use only in this context, as will become apparent from the following summaries and detailed descriptions of aspects, features, and one or more embodiments of the present invention.

Accordingly, one aspect of the present invention relates to a method for facilitating editing of a toggle item. The method includes displaying, to a user via a display associated with an electronic device, an interface comprising one or more toggle items, each toggle item being configured to be toggled on and off when clicked on; receiving, from the user via a mouse associated with the electronic device, input corresponding to movement of a mouse pointer to be disposed over a first toggle item of the one or more toggle items; determining, at the electronic device, that a predetermined amount of time has passed with the mouse pointer being disposed over the first toggle item; displaying, to the user on the interface via the display, a cursor in the first toggle item at the location of the mouse pointer; receiving, from the user via the mouse associated with the electronic device, input corresponding to clicking of the mouse while the cursor is displayed in the first toggle item; receiving, from the user via one or more input devices associated with the electronic device, input corresponding to editing of the first toggle item; and updating, based on the input corresponding to editing of the toggle item, the text of the toggle item.

In a feature of this aspect, the electronic device comprises a desktop computer.

In a feature of this aspect, the electronic device comprises an all in one computer.

In a feature of this aspect, the electronic device comprises a laptop computer.

In a feature of this aspect, the display comprises a monitor.

In a feature of this aspect, the display comprises a display of a laptop computer.

In a feature of this aspect, the electronic device comprises a slate computer.

In a feature of this aspect, the electronic device comprises a Microsoft Surface.

In a feature of this aspect, the interface comprises an interface of a healthcare application.

In a feature of this aspect, the interface comprises an interface of an electronic health records application.

In a feature of this aspect, the method further comprises saving data indicating the updated text of the item to a data store.

In a feature of this aspect, receiving input corresponding to editing of the first toggle item comprises receiving input corresponding to deletion of one or more characters from the text of the first toggle item.

In a feature of this aspect, receiving input corresponding to editing of the first toggle item comprises receiving input corresponding to addition of one or more characters to the text of the first toggle item.

Another aspect relates to a method for facilitating editing of a toggle item. The method includes displaying, to a user via a display associated with an electronic device, an interface comprising one or more toggle items, each toggle item being configured to be toggled on and off when clicked on; receiving, from the user via a mouse associated with the electronic device, input corresponding to movement of a mouse pointer to be disposed over a first toggle item of the one or more toggle items; receiving, from the user via the mouse associated with the electronic device, first input corresponding to clicking of the mouse while the mouse pointer is disposed over the first toggle item; updating, based on the first input corresponding to clicking of the mouse while the mouse pointer is disposed over the first toggle item, the interface to indicate that the toggle item is toggled on; determining, at the electronic device, that a predetermined amount of time has passed with the mouse pointer being disposed over the first toggle item; displaying, to the user on the interface via the display, a cursor in the first toggle item at the location of the mouse pointer; receiving, from the user via the mouse associated with the electronic device, input corresponding to clicking of the mouse while the cursor is displayed in the first toggle item; receiving, from the user via one or more input devices associated with the electronic device, input corresponding to editing of the first toggle item; and updating, based on the input corresponding to editing of the toggle item, the text of the toggle item.

Another aspect relates to a method for facilitating editing of a toggle item. The method includes displaying, to a user via a display associated with an electronic device, an interface comprising one or more toggle items, each toggle item being configured to be toggled on and off when clicked on; receiving, from the user via an input device associated with the electronic device, input corresponding to movement of a pointer to be disposed over a first toggle item of the one or more toggle items; determining, at the electronic device, that a predetermined amount of time has passed with the pointer being disposed over the first toggle item; displaying, to the user on the interface via the display, a cursor in the first toggle item at the location of the pointer; receiving, from the user via the input device associated with the electronic device, input corresponding to a click while the cursor is displayed in the first toggle item; receiving, from the user via one or more input devices associated with the electronic device, input corresponding to editing of the first toggle item; and updating, based on the input corresponding to editing of the toggle item, the text of the toggle item.

In a feature of this aspect, the input device comprises a trackball.

In a feature of this aspect, the input device comprises a trackpad.

In a feature of this aspect, the input device comprises a controller.

In a feature of this aspect, the input device comprises a remote control.

Another aspect relates to one or more non-transitory computer readable media containing instructions configured for performing a disclosed method.

Another aspect relates to a system for performing a disclosed method.

Another aspect relates to software for a disclosed method.

In addition to the aforementioned aspects and features of the present invention, it should be noted that the present invention further encompasses the various possible combinations and subcombinations of such aspects and features. Thus, for example, any aspect may be combined with an aforementioned feature in accordance with the present invention without requiring any other aspect or feature.

BRIEF DESCRIPTION OF THE DRAWINGS

One or more preferred embodiments of the present invention now will be described in detail with reference to the accompanying drawings, wherein the same elements are referred to with the same reference numerals, and wherein.

FIG. 2 illustrates highlighting of a toggle item based on the location of a mouse pointer;

FIG. 3 illustrates toggling of a toggle item;

FIG. 5 illustrates toggling of a toggle item;

DETAILED DESCRIPTION

Figure 1:
FIG. 1 illustrates an exemplary interface in accordance with one or more preferred implementations.

As a preliminary matter, it will readily be understood by one having ordinary skill in the relevant art ("Ordinary Artisan") that the present invention has broad utility and application. As should be understood, any embodiment may incorporate only one or a plurality of the above-disclosed aspects of the invention and may further incorporate only one or a plurality of the above-disclosed features. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention in any claim of a patent issuing here from, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the issued claim(s) rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. 112, paragraph 6 or subsection (f), no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, one or more preferred embodiments of the present invention are next described. The following description of one or more preferred embodiments is merely exemplary in nature and is in no way intended to limit the invention, its implementations, or uses.

As noted above, toggle controls are useful interface tools, and due to their usefulness in a narrative text description, there is the potential to want to edit or add free text as part of an item that can be toggled, but there is a problem in that the fastest, most desired method to insert a cursor to add free text is to click on the location for the cursor.

In accordance with one or more preferred implementations, an interface is configured to present one or more toggle controls comprising a plurality of toggle items and configured such that, if a user hovers on top of one of the toggle items, a cursor is presented which allows a user to add text to, or edit the text of, the toggle item without losing the ability to continue to toggle the item.

Preferably, when a user hovers over a toggle item with a mouse pointer, the toggle item is highlighted and, after a short delay, a cursor appears at the location of the mouse pointer. Preferably, the user can move the cursor with his or her mouse, and once the cursor is in a location that the user desires, the user can click to drop the cursor in place and then begin typing text to add free text, or use backspace or delete to delete text. Preferably, if a user is hovering over one item with the cursor available and moves the mouse pointer to another toggle item directly, the cursor will immediately appear in the item (without delay) and the user can click to drop the cursor in that location.

FIG. 1 illustrates an exemplary interface in accordance with one or more preferred implementations. The interface includes a plurality of toggle items, including toggle items for "Fever", "Chills", and "Body Aches", as well as toggle items for indicating when a patient was last seen.

Figure 2:
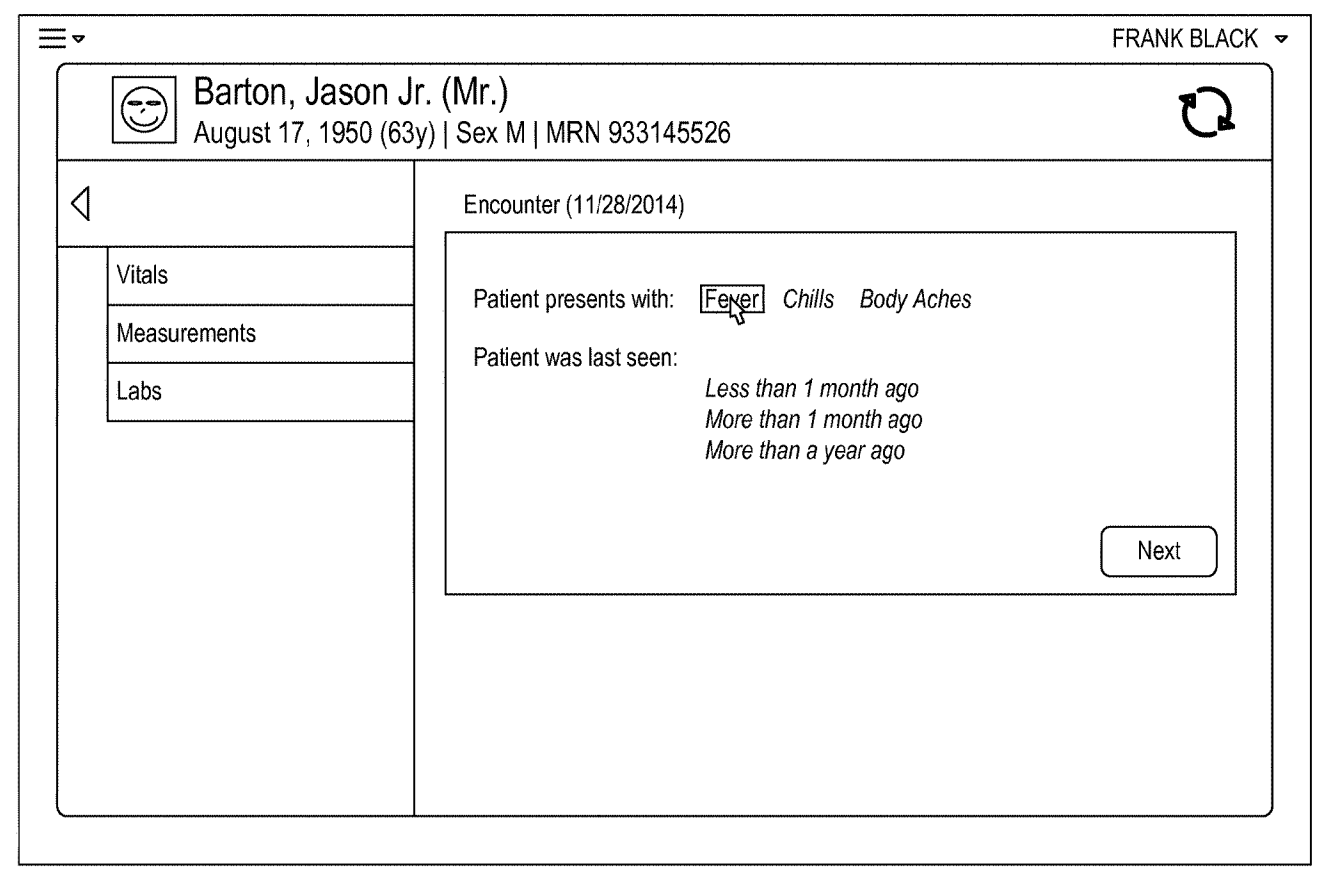

When a user utilizes a mouse to move a mouse pointer over one of the toggle items, that toggle item is highlighted, as illustrated in FIG. 2. The user can then click on the toggle item to toggle it to a different state, as illustrated in FIG. 3, where a user has toggled the "Fever" toggle item to indicate that a patient has a fever.

Figure 4:
FIG. 4 illustrates hovering of a mouse pointer over a toggle item.

A user can utilize the mouse to hover the mouse pointer over one of the toggle items, as illustrated in FIG. 4, where the user hovers the mouse pointer over a "More than a year ago" toggle item. While hovering, the user can click on the toggle item to toggle it, as illustrated in FIG. 5.

Figure 6:
FIG. 6 illustrates presentation of a cursor within a toggle item based on hovering over the toggle item.
Figure 7:
FIG. 7 illustrates editing of a toggle item.
Figure 8:
FIG. 8 illustrates a toggle item that has been edited.

If the user continues to hover over a toggle item (either with or without having clicked on it) for a predetermined period of time, then a cursor will appear in the toggle item, as illustrated in FIG. 6. The user can then edit the toggle item as illustrated in FIG. 7, resulting in use of a custom toggle item, as illustrated in FIG. 8.

Preferably, upon editing of a toggle item, the edited text of the toggle item is not just displayed, but is additionally utilized as a value for communication and storage of data regarding the toggle item.

Figure 9:
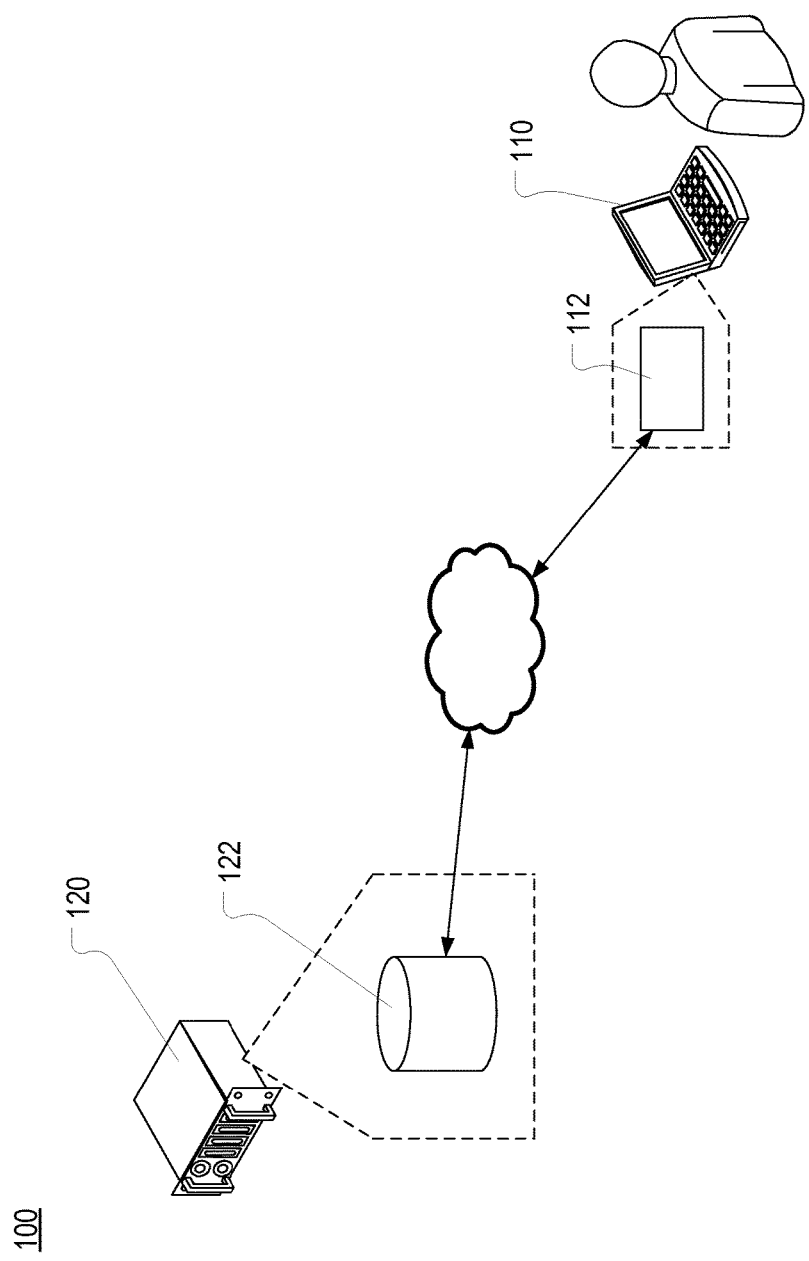
FIG. 9 illustrates a system in which changes made by a user to a toggle item of an interface of an application loaded on a computer result in communication of data indicating the new text value of the toggle item via the internet to a server where the data is saved in a data store.

For example, FIG. 9 illustrates a system 100 in which changes made by a user to a toggle item of an interface of an application loaded on a computer 110 result in communication of data indicating the new text value of the toggle item via the internet to a server 120 where the data is saved in a data store 122.

Figure 10:
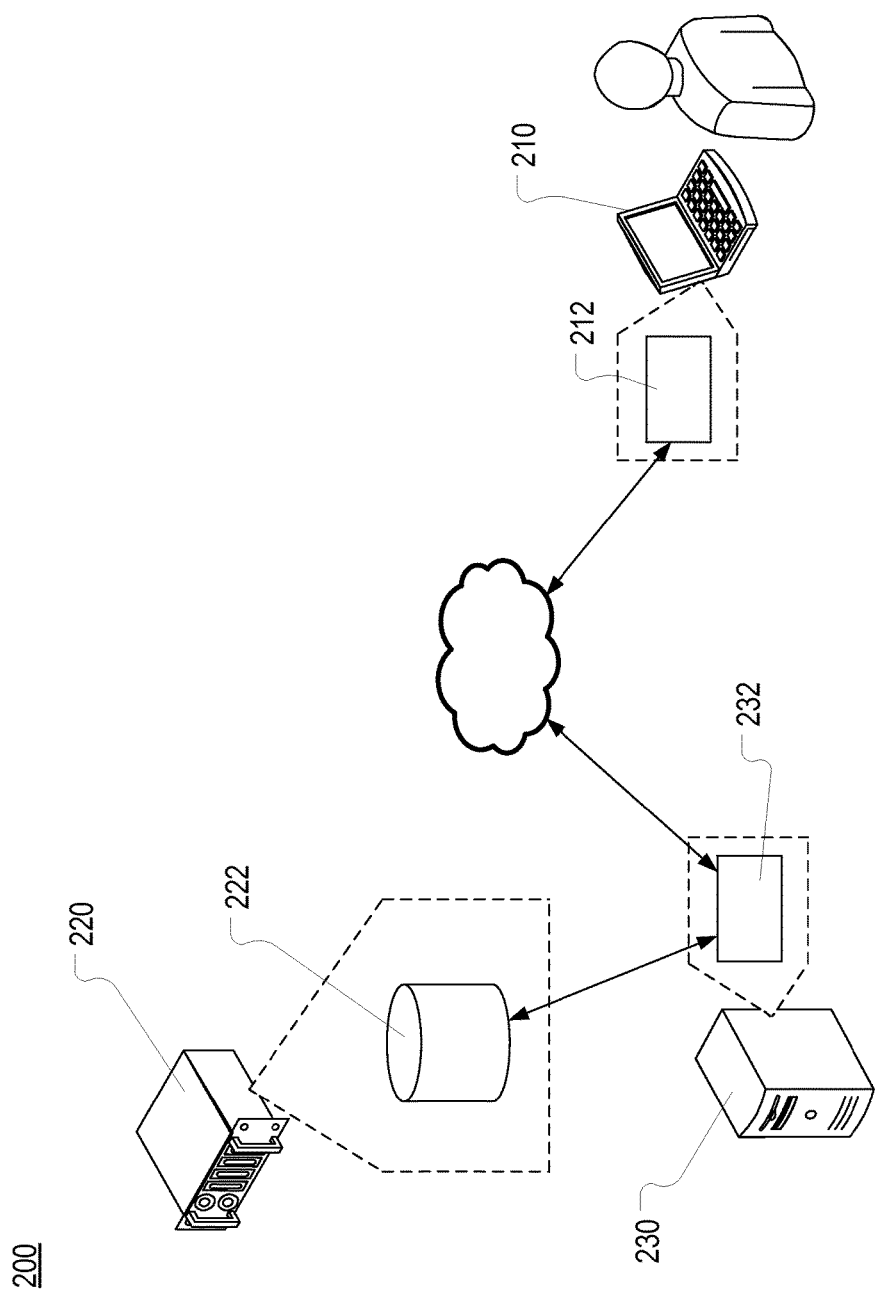
FIG. 10 illustrates another system in which an interface of an application at a server including one or more toggle items is displayed on a monitor associated with a computer.

FIG. 10 illustrates another system 200 in which an interface of an application 232 at a server 230 (e.g. a web/cloud application) including one or more toggle items is displayed on a monitor associated with a computer 210, and changes made by a user to one of the toggle items results in communication of data indicating the new text value of the toggle item and saving of an indication of the value at a data store 222 at another server 220. In one or more preferred implementations, the interface may be accessed at the computer 210 via an application 212, such as a thin client application or a web browser.

Figure 11:
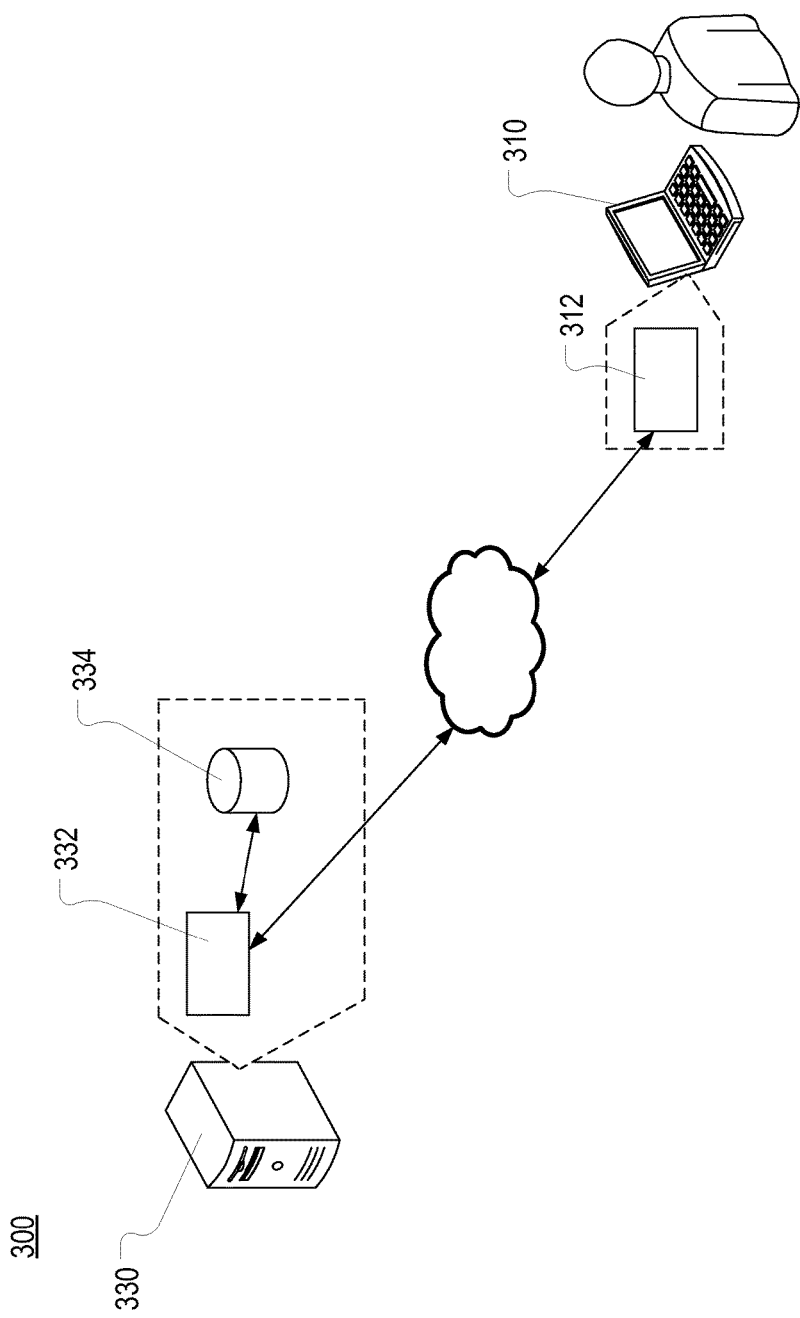
FIG. 11 illustrates another system in which an interface of an application at a server including one or more toggle items is displayed on a monitor associated with a computer.

FIG. 11 illustrates another system 300 in which an interface of an application 332 at a server 330 (e.g. a web/cloud application) including one or more toggle items is displayed on a monitor associated with a computer 210, and changes made by a user to one of the toggle items results in communication of data indicating the new text value of the toggle item and saving of an indication of the value at a data store 334 at the server 330. In one or more preferred implementations, the interface may be accessed at the computer 310 via an application 312, such as a thin client application or a web browser.

It will be appreciated that these are merely exemplary systems, and that methods and functionality disclosed herein may be implemented in a variety of manners in a variety of systems.

In one or more preferred implementations, user input may be provided via a keyboard, mouse, trackball, touchpad, touchscreen, gaming controller, joystick, or other input device.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention. Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

What is claimed is:

1. A method for facilitating editing of a toggle item, the method comprising:
  (a) displaying, to a user via a display associated with an electronic device, an interface comprising one or more toggle items, each toggle item being configured to be toggled on and off when clicked on;

(b) receiving, from the user via a mouse associated with the electronic device, input corresponding to movement of a mouse pointer to be disposed over a first toggle item of the one or more toggle items;

(c) receiving, from the user via the mouse associated with the electronic device, first input corresponding to clicking of the mouse while the mouse pointer is disposed over the first toggle item;

(d) updating, based on the first input corresponding to clicking of the mouse while the mouse pointer is disposed over the first toggle item, the interface to indicate that the toggle item is toggled on;

(e) determining, at the electronic device, that a predetermined amount of time has passed with the mouse pointer being disposed over the first toggle item;

(f) displaying, to the user on the interface via the display, a cursor in the first toggle item at the location of the mouse pointer;

(g) receiving, from the user via the mouse associated with the electronic device, input corresponding to clicking of the mouse while the cursor is displayed in the first toggle item;

(h) receiving, from the user via one or more input devices associated with the electronic device, input corresponding to editing of the first toggle item; and (i) updating, based on the input corresponding to editing of the toggle item, the text of the toggle item.

2. The method of claim 1, wherein the electronic device comprises a desktop computer.

3. The method of claim 1, wherein the electronic device comprises an all in one computer.

4. The method of claim 1, wherein the electronic device comprises a laptop computer.

5. The method of claim 1, wherein the display comprises a monitor.

6. The method of claim 1, wherein the display comprises a display of a laptop computer.

7. The method of claim 1, wherein the electronic device comprises a slate computer.

8. The method of claim 1, wherein the electronic device comprises a Microsoft Surface.

9. The method of claim 1, wherein the interface comprises an interface of a healthcare application.

10. The method of claim 1, wherein the interface comprises an interface of an electronic health records application.

11. The method of claim 1, wherein the method further comprises saving data indicating the updated text of the item to a data store.

12. The method of claim 1, wherein receiving input corresponding to editing of the first toggle item comprises receiving input corresponding to deletion of one or more characters from the text of the first toggle item.

13. The method of claim 1, wherein receiving input corresponding to editing of the first toggle item comprises receiving input corresponding to addition of one or more characters to the text of the first toggle item.

14. The method of claim 1, wherein the input device comprises a trackball.

15. The method of claim 1, wherein the input device comprises a trackpad.

16. The method of claim 1, wherein the input device comprises a controller.

17. The method of claim 1, wherein the input device comprises a remote control.

* * * * *